(12) United States Patent
Henry et al.

(10) Patent No.: US 8,892,371 B2
(45) Date of Patent: *Nov. 18, 2014

(54) WET GAS MEASUREMENT

(75) Inventors: Manus P. Henry, Oxford (GB); Michael S. Tombs, Oxford (GB)

(73) Assignee: Invensys Systems, Inc., Foxboro, MA (US)

( * ) Notice: Subject to any disclaimer, the term of this patent is extended or adjusted under 35 U.S.C. 154(b) by 1595 days.

This patent is subject to a terminal disclaimer.

(21) Appl. No.: 11/936,470

(22) Filed: Nov. 7, 2007

(65) Prior Publication Data
US 2008/0257066 A1 Oct. 23, 2008

Related U.S. Application Data

(60) Provisional application No. 60/913,148, filed on Apr. 20, 2007, provisional application No. 60/977,537, filed on Oct. 4, 2007.

(51) Int. Cl.
G01F 17/00 (2006.01)
G01F 1/84 (2006.01)
G01N 9/00 (2006.01)

(52) U.S. Cl.
CPC .............. *G01F 1/8486* (2013.01); *G01F 1/849* (2013.01); *G01N 2009/006* (2013.01); *G01N 9/002* (2013.01); *G01F 1/8436* (2013.01)
USPC .................................. 702/50; 702/45; 702/54

(58) Field of Classification Search
USPC ................................. 702/45, 50, 54
See application file for complete search history.

(56) References Cited

U.S. PATENT DOCUMENTS

| 5,029,482 | A | 7/1991 | Liu et al. |
| 5,224,372 | A | 7/1993 | Kolpak |
| 5,224,387 | A | 7/1993 | Lindenbaum et al. |
| 5,230,254 | A | 7/1993 | Craft |
| 5,259,250 | A | 11/1993 | Kolpak |
| 5,594,180 | A | 1/1997 | Carpenter et al. |
| 5,861,561 | A * | 1/1999 | Van Cleve et al. ......... 73/861.52 |
| 6,318,156 | B1 | 11/2001 | Dutton et al. |
| 6,327,914 | B1 | 12/2001 | Dutton |

(Continued)

OTHER PUBLICATIONS

International Search Report and Written Opinion for International Application No. PCT/US08/60863, mailed Jul. 30, 2008, 11 pages.

(Continued)

*Primary Examiner* — Elias Desta
(74) *Attorney, Agent, or Firm* — Edward S. Jarmolowicz, Esq.

(57) ABSTRACT

A first apparent property of a multi-phase process fluid is determined based on the motion of the vibratable flowtube. One or more apparent intermediate values associated with the process fluid are determined based on the first apparent property. One or more corrected intermediate values are determined based on a mapping between the apparent intermediate values and the corrected intermediate values. One or more phase-specific properties of the multi-phase process fluid are determined based on the corrected intermediate values. A measure of wetness of the multi-phase process fluid is determined based on the one or more phase-specific properties that are determined based on the corrected intermediate values. A second apparent property of the multi-phase process fluid is determined using the differential pressure flowmeter. A phase-specific property of a phase of the multi-phase process fluid is determined based on the measure of wetness and the second apparent property.

30 Claims, 7 Drawing Sheets

(56) References Cited

U.S. PATENT DOCUMENTS

| | | |
|---|---|---|
| 6,345,536 B1 | 2/2002 | Morrison et al. |
| 6,422,092 B1 | 7/2002 | Morrison et al. |
| 7,032,432 B2 | 4/2006 | Gysling et al. |
| 7,040,181 B2 | 5/2006 | Rieder et al. |
| 7,096,719 B2 | 8/2006 | Gysling |
| 7,134,320 B2 | 11/2006 | Gysling et al. |
| 7,152,460 B2 | 12/2006 | Gysling et al. |
| 7,165,464 B2 | 1/2007 | Gysling et al. |
| 7,299,705 B2 | 11/2007 | Gysling |
| 7,328,624 B2 | 2/2008 | Gysling et al. |
| 7,337,075 B2 | 2/2008 | Gysling et al. |
| 7,343,818 B2 | 3/2008 | Gysling et al. |
| 7,357,039 B2 | 4/2008 | Rieder et al. |
| 7,367,240 B2 | 5/2008 | Gysling et al. |
| 7,380,438 B2 | 6/2008 | Gysling et al. |
| 7,380,439 B2 | 6/2008 | Gysling et al. |
| 7,389,687 B2 | 6/2008 | Gysling et al. |
| 2004/0069069 A1 | 4/2004 | Gysling |
| 2005/0081643 A1* | 4/2005 | Mattar et al. .............. 73/861.355 |
| 2005/0193832 A1 | 9/2005 | Tombs |
| 2005/0229716 A1 | 10/2005 | Unsworth et al. |
| 2005/0284237 A1 | 12/2005 | Henry et al. |
| 2006/0217899 A1* | 9/2006 | Unsworth et al. .............. 702/45 |
| 2007/0006744 A1 | 1/2007 | Gysling |

OTHER PUBLICATIONS

International Search Report and Written Opinion for corresponding International Application No. PCT/US08/60843, mailed Jun. 4, 2009.

Falcone, G., and Alimonti, C., "Critical Review of Wet Gas Definitions," *24th International North Sea Flow Measurement Workshop*, Oct. 24-27, 2006, p. 5, retrieved on May 24, 2009 from http://energytechnologycentre.com/upload/pdfs/NSFMW06a.pdf.

Office Action for U.S. Appl. No. 11/936,519, mailed Jul. 1, 2009, 16 pages.

\* cited by examiner

WET GAS MEASUREMENT

CROSS-REFERENCE TO RELATED APPLICATIONS

This application claims priority to U.S. Provisional Application Ser. No. 60/913,148, titled WET GAS CALCULATIONS, and filed on Apr. 20, 2007, and U.S. Provisional Application Ser. No. 60/977,537, titled WET GAS MEASUREMENT, and filed on Oct. 4, 2007, both of which are incorporated by reference.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, densitometers provide a measurement of the density of material flowing through a conduit. Mass flowmeters also may provide a measurement of the density of the material.

For example, Coriolis-type mass flowmeters are based on the Coriolis effect, in which material flowing through a conduit becomes a radially-travelling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

In one general aspect, a multi-phase process fluid is passed through a vibratable flowtube and a differential pressure flowmeter. Motion is induced in the vibratable flowtube. A first apparent property of the multi-phase process fluid is determined based on the motion of the vibratable flowtube. One or more apparent intermediate values associated with the multi-phase process fluid are determined based on the first apparent property. One or more corrected intermediate values are determined based on a mapping between the apparent intermediate values and the corrected intermediate values. One or more estimated phase-specific properties of the multi-phase process fluid are determined based on the corrected intermediate values. A measure of wetness of the multi-phase process fluid is determined based on the one or more estimated phase-specific properties. A second apparent property of the multi-phase process fluid is determined using the differential pressure flowmeter. A corrected phase-specific property of a phase of the multi-phase process fluid is determined based on the measure of wetness and the second apparent property.

Implementations may include one or more of the following features. The mapping may be a neural network. The multi-phase process fluid may be a wet gas. Determining the first apparent property of the multi-phase process fluid may include determining a third apparent property of the multi-phase process fluid based on the motion of the vibratable flowtube. Determining one or more apparent intermediate values associated with the multi-phase process fluid based on the first apparent property may include determining one or more apparent intermediate values associated with the multi-phase process fluid based on the first apparent property and the third apparent property. The first apparent property of the multi-phase process fluid may be an apparent bulk mass flowrate of the multi-phase process fluid and the third apparent property may be an apparent bulk density of the multi-phase process fluid. Determining one or more apparent intermediate values associated with the multi-phase process fluid based on the first apparent property may include determining a volume fraction of the multi-phase process fluid and a volumetric flowrate of the multi-phase process fluid.

One or more measurements corresponding to an additional property of the process fluid may be received. The additional property of the multi-phase process fluid may include one or more of a temperature of the multi-phase process fluid, a pressure associated with the multi-phase process fluid, or a water-cut of the multi-phase process fluid.

Determining one or more apparent intermediate value associated with the multi-phase process fluid based on the first apparent property may include determining the one or more apparent intermediate values based on the first apparent property and the additional property.

The measure of wetness may be a Lockhart-Martinelli parameter. The second apparent property may be a mass flowrate of the multi-phase process fluid as a dry gas. The differential pressure flowmeter may be an orifice plate. Determining a phase-specific property of the multi-phase process fluid based on the measure of wetness and the second apparent property may include determining a mass flowrate of a gas phase of the multi-phase process fluid.

Implementations of any of the techniques described above may include a method or process, a system, a flowmeter, or instructions stored on a storage device of flowmeter transmitter. The details of particular implementations are set forth in the accompanying drawings and description below. Other features will be apparent from the following description, including the drawings, and the claims.

DETAILED DESCRIPTION

Types of flowmeters include digital Coriolis flowmeters. For example, U.S. Pat. No. 6,311,136, which is hereby incorporated by reference, discloses the use of a digital Coriolis flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital Coriolis flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow (e.g., a flow containing a mixture of liquid and gas).

Although digital Coriolis flowmeters are specifically discussed below with respect to, for example, FIGS. 1A, 1B and 2, it should be understood that analog Coriolis flowmeters also exist. Although such analog Coriolis flowmeters may be prone to typical shortcomings of analog circuitry, e.g., low precision and high noise measurements relative to digital Coriolis flowmeters, they also may be compatible with the various techniques and implementations discussed herein. Thus, in the following discussion, the term "Coriolis flowmeter" or "Coriolis meter" is used to refer to any type of device and/or system in which the Coriolis effect is used to measure a mass flowrate, density, and/or other parameters of a material(s) moving through a flowtube or other conduit.

Figure 1A:
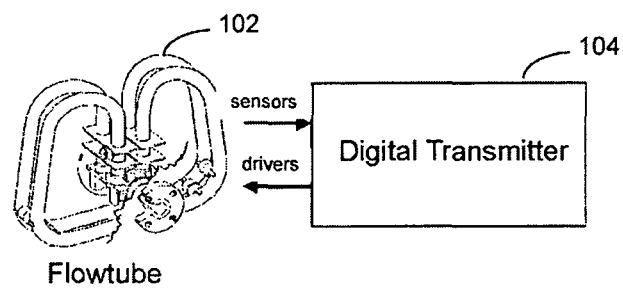
FIG. 1A is an illustration of a Coriolis flowmeter using a bent flowtube.

FIG. 1A is an illustration of a digital Coriolis flowmeter using a bent flowtube 102. Specifically, the bent flowtube 102 may be used to measure one or more physical characteristics of, for example, a (travelling or non-travelling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, may provide for fast and accurate operation of the bent flowtube 102. Examples of the digital transmitter 104 being used with a bent flowtube are provided in, for example, commonly-assigned U.S. Pat. No. 6,311,136.

Figure 1B:
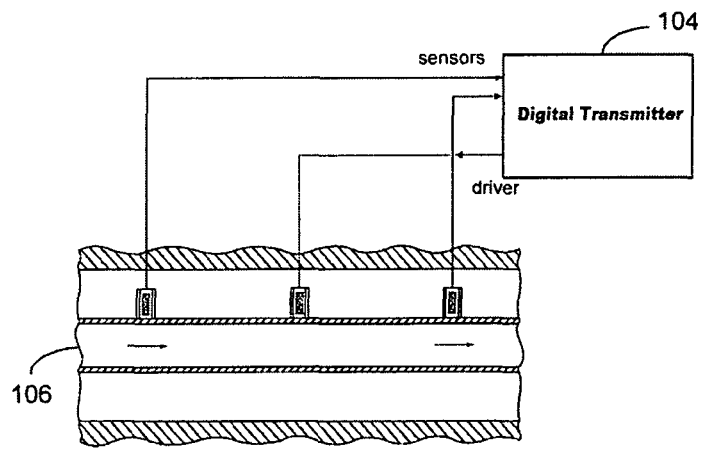
FIG. 1B is an illustration of a Coriolis flowmeter using a straight flowtube.

FIG. 1B is an illustration of a digital Coriolis flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz. The bent flowtube 102 represents flowtubes having a variety of diameters, and may be operated in multiple orientations, such as, for example, in a vertical or horizontal orientation. The straight flowtube 106 also may have a variety of diameters, and may be operated in multiple orientations.

Figure 2:
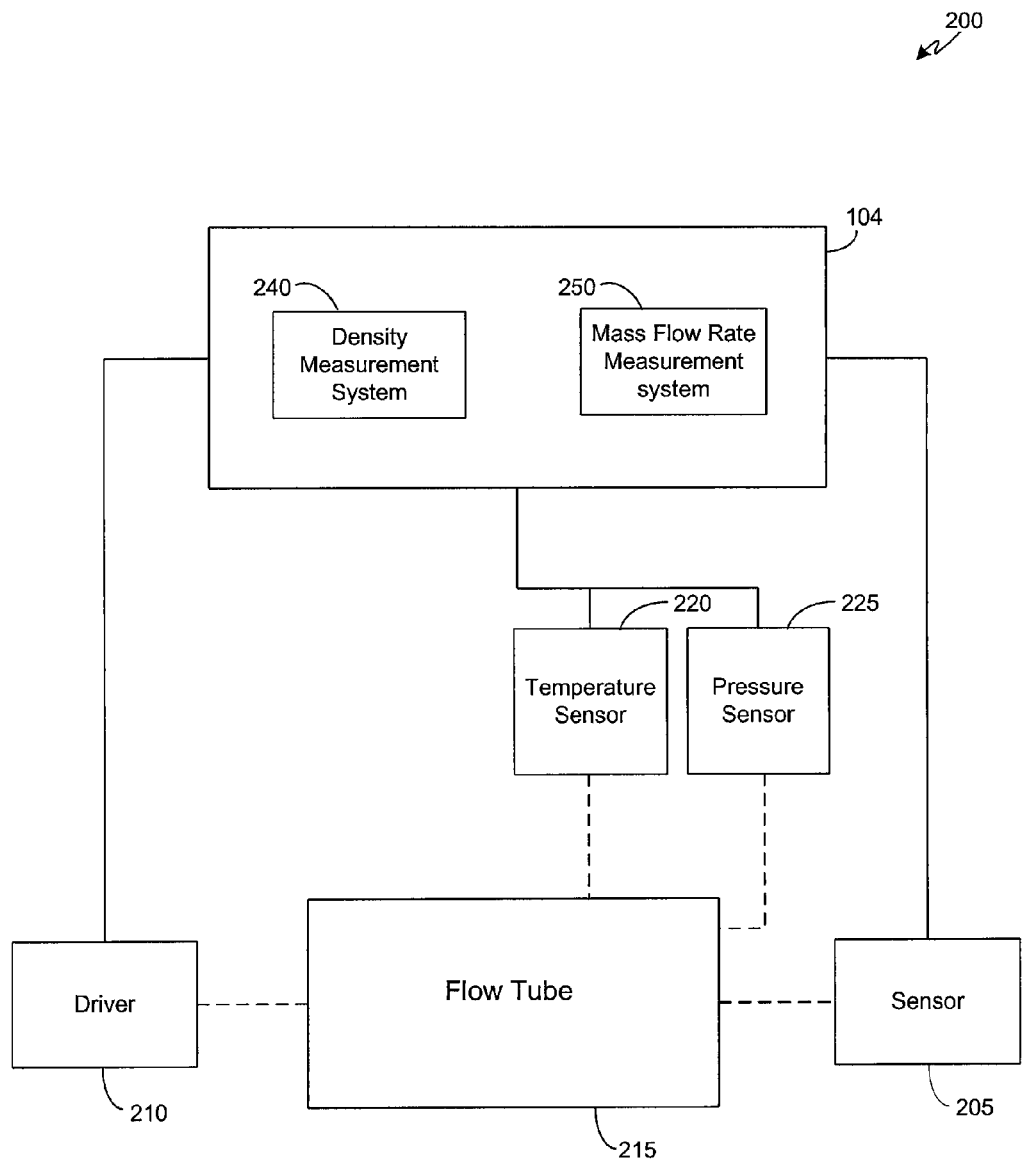
FIG. 2 is a block diagram of a Coriolis flowmeter.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), a temperature sensor 220, and a pressure sensor 225. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. It should be understood that, as described in U.S. Pat. No. 6,311,136, associated digital-to-analog converters may be included for operation of the drivers 210, while analog-to-digital converters may be used to convert sensor signals from the sensors 205 for use by the digital transmitter 104.

The digital transmitter 104 may include a bulk density measurement system 240 and a bulk mass flowrate measurement system 250. Bulk properties generally refer to properties of the fluid as a whole, as opposed to the properties of a constituent component of the fluid when multi-phase flow is present (as described below). Density measurement system 240 and mass flowrate measurement system 250 may generate measurements of, respectively, density and/or mass flowrate of a material flowing through the flowtube 215 based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 (typically the resonant frequency) by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

It should be understood that both the pressure of the fluid entering the flowtube 215 and the pressure drop across relevant points on the flowtube may be indicators of certain flow conditions. Also, while external temperature sensors may be used to measure the fluid temperature, such sensors may be used in addition to an internal flowmeter sensor designed to measure a representative temperature for flowtube calibrations. Also, some flowtubes use multiple temperature sensors for the purpose of correcting measurements for an effect of differential temperature between the process fluid and the environment (e.g., a case temperature of a housing of the flowtube).

In FIG. 2, it should be understood that the various components of the digital transmitter 104 are in communication with one another, although communication links are not explicitly illustrated, for the sake of clarity. Further, it should be understood that conventional components of the digital transmitter 104 are not illustrated in FIG. 2, but are assumed to exist within, or be accessible to, the digital transmitter 104. For example, the digital transmitter 104 will typically include drive circuitry for driving the driver 210, and measurement circuitry to measure the oscillation frequency of the flowtube 215 based on sensor signals from sensors 205 and to measure the phase between the sensor signals from sensors 205.

Under certain conditions, a Coriolis flowmeter can accurately determine the bulk density and bulk mass flowrate of a process fluid in the flowtube 215. That is, an accurate bulk density and/or bulk mass flowrate of the process fluid can be determined under certain conditions.

Also, in some situations, the process fluid may contain more than one phase by being a mixture of two or more materials (for example, oil and water or a fluid with entrained gas), by being the same material in different phases (for example, liquid water and water vapor), or by being different materials in different phases (for example, water vapor and oil). In some multi-phase flow conditions, a Coriolis flowmeter may accurately determine the bulk density and bulk mass flowrate of the fluid, which can then be used to accurately determine the density and/or mass flowrate of the constituent phases.

Under other multi-phase flow conditions, however, a Coriolis flowmeter may not perform in a satisfactory manner. Although the Coriolis flowmeter continues to operate in the presence of the multi-phase process fluid, the presence of the multi-phase fluid affects the motion of the flowtube (or conduit) that is part of the Coriolis flowmeter. Thus, the outputs determined by the meter may be inaccurate because the meter operates on the assumption that the process fluid is either single phase, or the process fluid is a multi-phase fluid with properties such as high liquid viscosity and/or no slip between phases. These outputs may be referred to as apparent properties because they have not been corrected for the effects of multi-phase flow. While apparent properties generally are those that have not been corrected for the effects of multi-phase flow, initial estimates of these properties may have been corrected for other effects to generate the apparent properties. For instance, initial estimates of these properties may be corrected for the effects of temperature and/or pressure on the properties to generate the apparent properties.

For instance, under some multi-phase flow conditions, a Coriolis flowmeter may not be able to measure the bulk density, the bulk mass flowrate, the density of constituent components of a multi-phase flow, or the mass flowrates of constituent components of a multi-phase flow within the required tolerances needed in a particular application because these properties are determined based on an assumption that single-phase flow is present, and the resulting errors introduced by multi-phase flow are greater than the required tolerances.

Examples of such conditions include situations in which the process fluid is a wet gas (that is, it contains mostly a gas component, but has some liquid component). A wet gas typically occurs in applications involving natural gas, where the gas component is the natural gas, and the liquid component may be water, hydrocarbons, or compressor oil (or some combination thereof). Other applications in which a wet gas occurs may include applications involving steam as the process fluid.

A wet gas generally includes a process fluid that contains 5% by volume or less of a liquid or, in other words, a process fluid that has a void fraction of 0.95 (95%) or more. However, the techniques described below with respect to wet gasses are not limited to process fluids that contain 5% by volume of less or a liquid. Rather, the techniques are bounded by the required accuracy of a given application, with the accuracy depending on the accuracy of the Coriolis flowmeter and other meters described below for a given void fraction.

Figure 3:
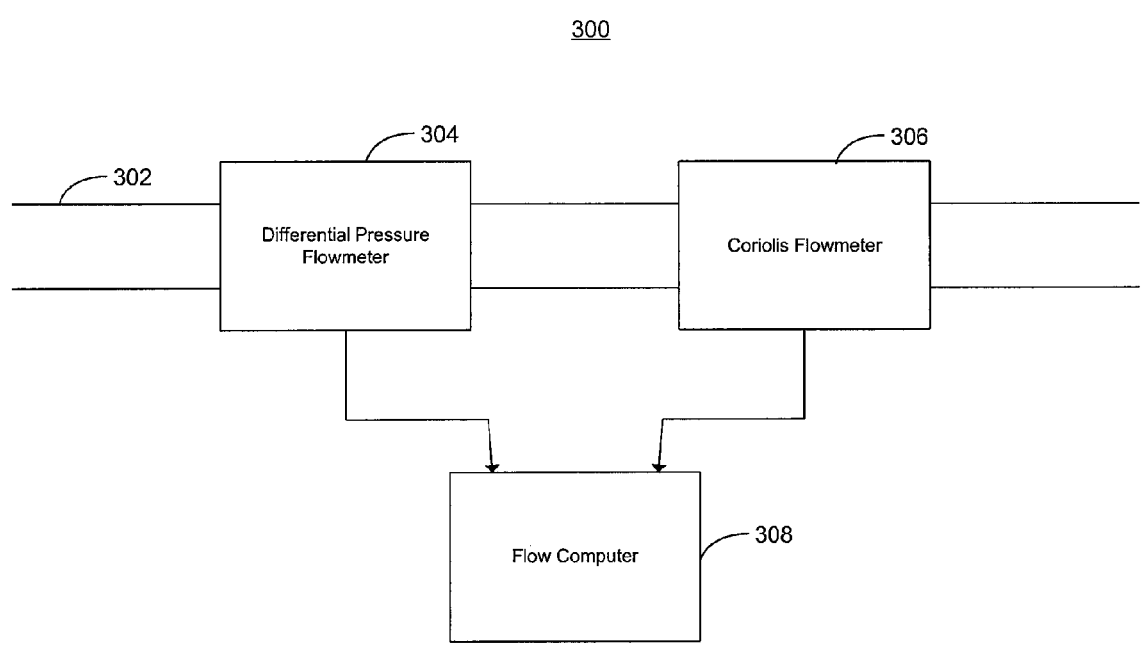
FIG. 3 is a block diagram showing a system that includes a differential pressure flowmeter and a Coriolis flowmeter.

Referring to FIG. 3, a differential pressure flowmeter 304 may be used in combination with a Coriolis flowmeter 306 to more accurately measure the properties of a wet gas or other multi-phase process fluid. As illustrated, a system 300 includes a conduit 302 that carries the process fluid (e.g., wet gas), a differential pressure flowmeter 304, a Coriolis flowmeter 306 that measures the apparent bulk mass flowrate and apparent bulk density of the process fluid, and a flow computer 308. In some implementations, the flow computer 308 may act as the transmitter 104 discussed above. In some implementations, the flow computer 308 may be separate from the differential pressure flowmeter 304 and the Coriolis flowmeter 306. In general, differential pressure flowmeters, such as the differential pressure flowmeter 304, guide the flow of a process fluid into a section of the differential pressure flowmeter 304 that has a cross sectional area different than the cross sectional area of the conduit that carries the process fluid. This results in variations of the flow velocity and the pressure. By measuring the changes in pressure, the flow velocity can be calculated. The bulk mass flowrate can be calculated from the flow velocity and the density of the bulk fluid. The density of the bulk fluid may be measured, calculated from pressure and temperature values, or otherwise determined. However, as with the Coriolis flowmeter, the calculations of bulk mass flowrate may be performed based on an assumption of single-phase flow, and therefore the measurement may be inaccurate when a multi-phase fluid is present. Hence, the bulk mass flowrate may be an apparent bulk mass flowrate because it has not been corrected to account for multi-phase flow.

In some implementations, the differential pressure flowmeter 304 may be an orifice plate. An orifice plate is typically a flat plate that includes an orifice. An orifice plate is normally mounted between a pair of flanges and is installed in a straight run of smooth pipe to avoid disturbance of flow patterns from fittings and valves.

Flow through an orifice plate is characterized by a change in velocity and pressure. The pressure of the fluid drops as it travels across the orifice plate. As the fluid passes through the orifice, the fluid converges, and the velocity of the fluid increases to a maximum value. At this point, the pressure is at a minimum value. As the fluid diverges to fill the entire pipe area, the velocity decreases back to the original value. Downstream from the orifice plate, the pressure increases relative to the pressure decrease that occurs from the fluid passing through the orifice plate. The pressure increases such that about 60% to 80% of the pressure drop is recovered. In other words, the pressure increases towards the original input value, typically recovering 60-80% of the maximum pressure drop. The pressures on both sides of the orifice are measured, resulting in a differential pressure, which is proportional to the flow velocity. From the velocity, the apparent bulk mass flowrate can be calculated for a known fluid density.

Thus, the differential pressure flowmeter 304 may be an orifice plate. The orifice plate may include the conduit 302 for carrying the process fluid and an orifice plate located in the conduit 302. An arrow 310 illustrates the direction of flow. Upstream from the orifice plate is a first pressure sensor and downstream from the orifice plate is a second pressure sensor. The difference between the measurements of the first sensor and the second sensor provides the differential pressure, which may be used to calculate the flow velocity and the apparent bulk mass flowrate.

The apparent bulk properties determine by the Coriolis flowmeter 306 and the differential pressure flowmeter 304 may be used to determine corrected values of, e.g., the mass flowrates of the constituent components of the fluid, as described further below.

Figure 4:
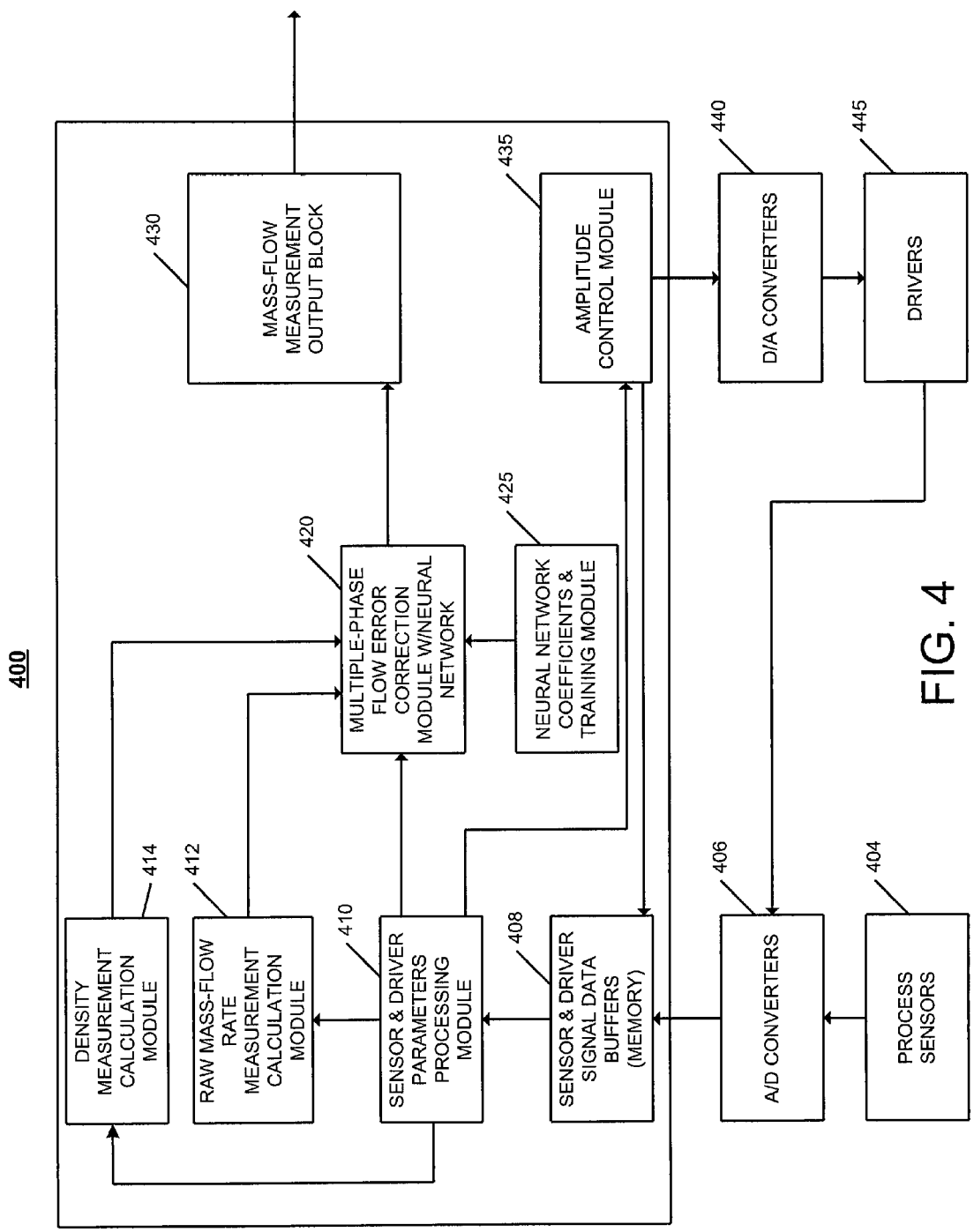
FIG. 4 is a block diagram of a digital controller implementing a neural network processor that may be used with the digital mass flowmeter for multiple-phase fluid flows.

To that end, and with reference to FIG. 4, Coriolis flowmeter 306 may use a digital controller 400 in place of the digital transmitter 104 described above with respect to FIGS. 1A, 1B, and 2. The digital controller 400 also may be referred to as a digital transmitter. In this implementation of the digital transmitter 104, process sensors 404 connected to the flowtube generate process signals including one or more sensor signals, one or more temperature signals, and one or more pressure signals. For example, the process sensors 404 may include the temperature sensor 220, the pressure sensor 225, and/or the motion sensors 205 described with respect to FIG. 2. The analog process signals are converted to digital signal data by A/D converters 406 and stored in sensor and driver signal data memory buffers 408 for use by the digital controller 400. The drivers 445 connected to the flowtube generate a drive current signal and may communicate this signal to the A/D converters 406. The drive current signal then is converted to digital data and stored in the sensor and driver signal data memory buffers 408. Generally, it is assumed that the digital drive signal generated by the A/D converters 406 produces a digital drive signal corresponding to the analog drive signal. In some implementations, the digital drive signal may be monitored to ensure that the digital drive signal has the appropriate amplitude, phase, and frequency characteristics (e.g., that the digital drive signal is an accurate representation of the analog drive signal). The drive voltage also may be monitored. The monitoring may be accomplished by an additional A/D channel. The data sampled by the additional A/D channel may be analyzed in a manner similar to that of the sensor data. This sampled data may be used for diagnostic purposes as well as for maintaining. Alternatively, a digital drive gain signal and a digital drive current signal may be generated by the amplitude control module 435 and communicated to the sensor and driver signal data memory buffers 408 for storage and use by the digital controller 400.

The digital process sensor and driver signal data are further analyzed and processed by a sensor and driver parameters processing module 410 that generates physical parameters including frequency, phase, current, damping and amplitude of oscillation. This information is provided to a raw bulk mass flow measurement module 412 and a raw bulk density measurement module 414. The raw mass flow measurement module 412 generates a raw bulk mass flowrate measurement signal that indicates the apparent bulk mass flowrate of the fluid. The raw bulk density measurement module 414 generates a raw bulk density measurement signal that indicates the apparent bulk density of the fluid.

A multiple-phase flow error correction module 420 receives, as input, the physical parameters from the sensor and driver parameters processing module 410, the raw bulk mass flowrate measurement signal, and the raw bulk density measurement 414. When the process fluid may contain a single-phase or multi-phase flow condition, a flow condition state may be detected, which causes the processing by the multiple-phase flow error correction module 420 when multi-phase flow is present, or skips processing by the multiple-phase flow error correction module 420 when single phase flow is present. However, if the process fluid involves a known two-phase (e.g., gas and liquid constituents), three-phase (e.g., gas and two-liquid constituents) or other multiple-phase flow (e.g., one or more gas and one or more liquid constituents), the determination of a flow condition state may not be necessary. In this example, the process fluid may be a wet-gas that is already known to include a gas volume fraction (gvf) and liquid volume fraction (lvf).

The multiple-phase flow error correction module 420 includes a mapping function such as a neural network that is used to help compensate for multi-phase flow conditions. The mapping function can be implemented in a software routine, or alternatively may be implemented as a separate programmed hardware processor.

The inputs to the mapping function may be apparent intermediate values determined from the apparent bulk mass flowrate measurement signal and the apparent bulk density measurement signal. In this implementation, the multiple-phase flow error correction module 420 determines apparent intermediate values from the raw bulk mass flowrate and apparent bulk density of the multi-phase process fluid. The apparent intermediate values are input into the mapping function and corrected for the effects of multi-phase flow. The corrected apparent intermediate values are output to a mass-flow measurement output block 430. In other implementations, the apparent (or raw) bulk mass-flow measurement and apparent bulk density may be input to the mapping function.

When a neural network is used, a neural network coefficients and training module 425 stores a predetermined set or sets of neural network coefficients that are used by the neural network processor for the correction described above. The neural network coefficients and training module 425 also may perform an online training function using training data so that an updated set of coefficients can be calculated for use by the neural network. While the predetermined set of neural network coefficients are generated through extensive laboratory testing and experiments based upon known two-phase, three-phase, or higher-phase mass-flowrates, the online training function performed by module 425 may occur at the initial commissioning stage of the flowmeter, or may occur each time the flowmeter is initialized.

The corrected intermediate values from the mapping function are input to the mass-flow measurement output block 430. Using the corrected intermediate values, the mass-flow measurement output block 430 determines estimates of phase-specific properties of the fluid, such as the mass flowrates of the constituent phases of the multi-phase fluid. The estimates are then used with measurements made by the differential pressure flowmeter 304 to determine accurate or corrected measurements of the phase-specific properties of the fluid, such as the mass flowrate of the constituent phases, as described further below. In some implementations, the measurement output block 430 validates the mass-flow measurements for the phases and may perform an uncertainty analysis to generate an uncertainty parameter associated with the validation.

The sensor parameters processing module 410 also inputs a damping parameter and an amplitude of oscillation parameter to an amplitude control module 435. The amplitude control module 435 further processes the damping parameter and the amplitude of oscillation parameter and generates digital drive signals. The digital drive signals are converted to analog drive signals by D/A converters 440 for operating the drivers 445 connected to the flowtube of the digital flowmeter. In some implementations, the amplitude control module 435 may process the damping parameter and the amplitude of oscillation parameter and generate analog drive signals for operating the drivers 445 directly.

Figure 5A:
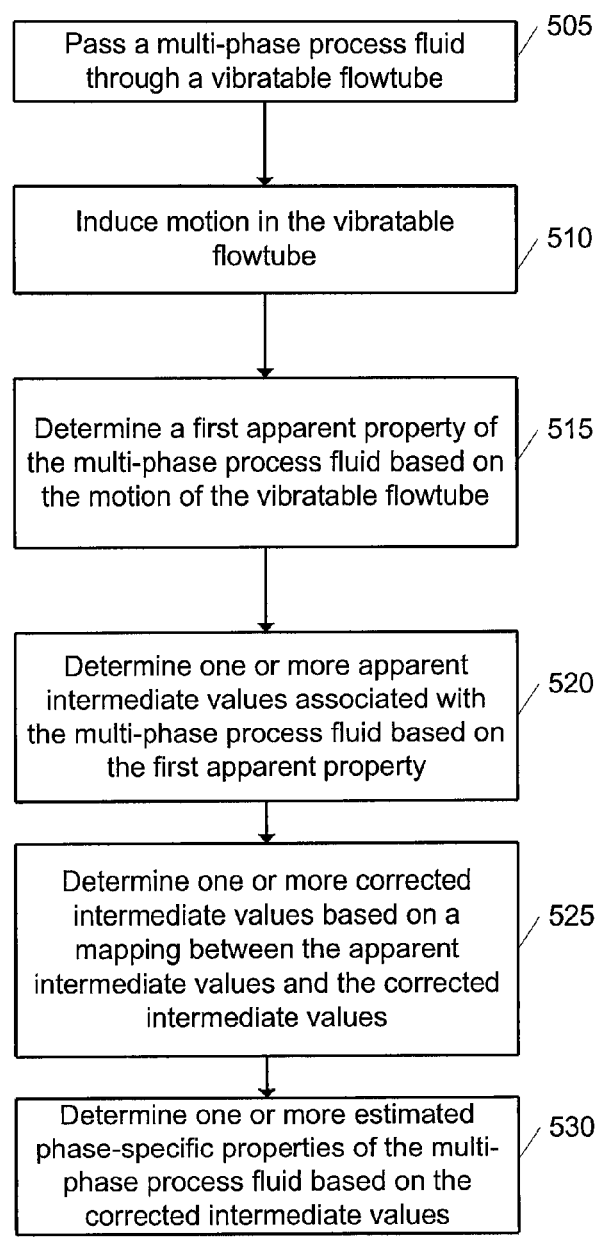
FIGS. 5A and 5B are flowcharts illustrating a process that employs a Coriolis flowmeter and a differential pressure flowmeter for multi-phase fluids.
Figure 5B:
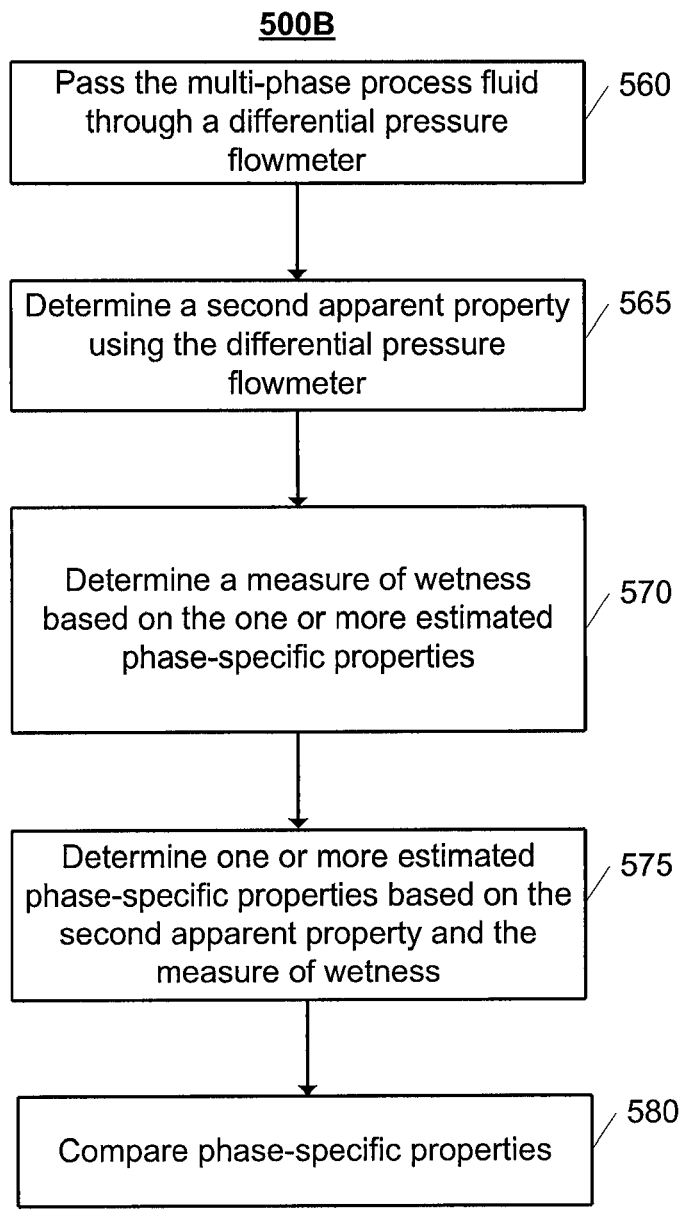

Referring to FIGS. 5A and 5B, example processes 500A and 500B may be implemented by system 300 and controller 400 to determine a corrected phase-specific property of a phase included in a multi-phase process fluid. For example, the processes 500A and 500B may be used to determine the mass flowrate of each phase of the multi-phase process fluid. The multi-phase process fluid may be, for example, a three-phase fluid such as a wet gas that includes a gas phase and two liquid phases (e.g., methane, water, and oil).

As described below, in one implementation, one or more apparent intermediate values are determined based on apparent or raw properties of the multi-phase fluid. For example, an apparent intermediate value may be determined based on an apparent bulk mass flowrate and/or an apparent bulk density of the multi-phase process fluid as determined by, for example, Coriolis flowmeter 306. The apparent intermediate value is input into, e.g., a neural network to produce a corrected intermediate value that accounts for the effects of the presence of a multi-phase process fluid. The corrected intermediate value is used to determine an estimate of phase-specific properties of the fluid, such as the mass flowrate of each of the phases of the multi-phase process fluid. Using an intermediate value rather than the apparent bulk mass flowrate and apparent bulk density of the multi-phase process fluid may help improve the accuracy of the determination of the estimated mass flowrate of each of the phases of the multiphase process fluid. The estimated phase-specific properties are then used to determine a measure of wetness of the multi-phase fluid. The measure of wetness is then used with measurements from the differential pressure flowmeter (e.g., orifice plate) to determine corrected values of phase-specific properties of the multi-phase fluid, such as the mass flowrates of the phases of the multi-phase fluid.

Referring specifically to FIG. 5A, a multi-phase process fluid is passed through the vibratable flowtube of Coriolis meter 306 (505). Motion is induced in the vibratable flowtube (510). The multi-phase fluid may be a two-phase fluid, a three-phase fluid, or a fluid that includes more than three phases. In general, each phase of the multi-phase fluid may be considered to be constituents or components of the multi-phase fluid. For example, a two-phase fluid may include a non-gas phase and a gas phase. The non-gas phase may be a liquid, such as oil, and the gas phase may be a gas, such as air. A three-phase fluid may include two non-gas phases and one gas phase. For example, the three-phase fluid may include a gas and two liquids such as water and oil. In another example, the three-phase fluid may include a gas, a liquid, and a solid (such as sand). Additionally, the multi-phase fluid may be a wet gas. While the wet gas may be any of the multi-phase fluids described above, wet gas is generally composed of more than 95% gas phase by volume. In general each phase of the multi-phase fluid may be referred to as constituents or components of the multi-phase fluid. The processes 500A and 500B may be applied to any multi-phase fluid.

A first apparent property of the multi-phase fluid is determined based on the motion of the vibratable flowtube (515). The first apparent property of the multi-phase fluid may be the apparent bulk mass flowrate and/or the apparent bulk density of the fluid flowing through the vibratable flowtube. As described above, an apparent property is one that has not been corrected for the effects the multi-phase fluid has on the motion of the flowtube. However, such properties may have been corrected for other effects to generate the apparent properties. For instance, initial estimates of these properties may be corrected for the effects of temperature and/or pressure on the properties to generate the apparent properties.

In general, additional information (e.g., the known densities of the materials in the individual phases) and/or additional measurements (e.g., pressure of the multi-phase fluid or the water-cut of the multi-phase fluid) may be used at times. Thus, in some implementations, in addition to properties determined based on the motion of the conduit, such as the first apparent property discussed above, additional or "external" properties of the multi-phase fluid such as temperature, pressure, and water-cut may be measured and used, e.g., as additional inputs to the mapping described below, to determine one or more apparent intermediate values as described below, or to help in determining the flowrates of the individual components of the multi-phase fluid. The additional properties may be measured by a device other than the flowmeter. For example, the water-cut of the multi-phase fluid, which represents the portion of the multi-phase fluid that is water, may be determined by a water-cut meter. The additional property also may include a pressure associated with the flowtube. The pressure associated with the flowtube may be, for example, a pressure of the multi-phase process fluid at an inlet of the flowtube and/or a differential pressure across the flowtube. The additional property may be the temperature of the multi-phase process fluid.

In some implementations, more than one apparent property may be determined based on the motion of the conduit. For example, in such an implementation, the apparent bulk mass flowrate of the multi-phase fluid and the apparent bulk density of the multi-phase fluid may be determined based on the motion of the conduit, and both of these apparent properties may be used to determine one or more apparent, intermediate values (such as liquid volume fraction and the volumetric flowrate, as described below). The following describes examples of how the apparent bulk mass flowrate and apparent bulk density can be determined.

The apparent bulk mass flowrate may be determined from the average of the apparent mass flowrate determined from the Coriolis meter, where the period of averaging is selected to represent a balancing between noise reduction due to two-phase effects on the one hand, and maintaining a dynamic response to genuine changes in the flowrate on the other. The averaging period may be, for example, 1 second. The following equation expresses the relationship between the average apparent mass flowrate and the apparent bulk mass flowrate:

$$m_m^a = \overline{m}_0.$$

The apparent mass flowrate from the Coriolis meter may be determined from the following equation, where $\phi$ is the observed phase angle difference of the flowtube 215 in degrees as measured by the sensors 205 (e.g., the phase difference between signals measured by the sensors 205), f is the observed frequency of the flowtube 215 in Hertz, T is the temperature of the flowtube 215 in degrees Celsius, A and B are flowtube-type specific temperature coefficients, $F_2$ is a flow calibration factor, and $F_f$ is a field-adjustable flowfactor (which has a nominal value of 1.000):

$$T_0 = 20° \ C.$$
$$\Delta T = T - T_0$$
$$m_0 = F_f \cdot F_2 (1 + A \cdot \Delta T + B \cdot \Delta T^2) \cdot \frac{6400}{f} \cdot \tan\left(\frac{\pi}{360}\phi\right).$$

The apparent bulk density of the multi-phase process fluid may be determined from the average of the apparent density determined from the Coriolis meter:

$$\rho_m^a = \overline{\rho}_p, \text{ where}$$
$$T_0 = 20.0° \ C.$$
$$\Delta T = T - T_0$$
$$\Delta P = P_i - P_0$$
$$\rho_0 = \frac{256}{f^2} \cdot D_2 \cdot (1 + C \cdot \Delta T) + D_4 \cdot (1 + D \cdot \Delta T)$$
$$\rho_p = \rho_0 + k_{pd} \cdot (P_i - P_0) + k_{dbias}.$$

In the above equation, $\rho_0$ is the raw density in kg/m³, $\rho_p$ is the pressure corrected density in kg/m³, $P_i$ barA is the inlet pressure of the flowtube 215, $P_0$ barA is a configured reference pressure, $k_{pd}$ kg/m³/bar and $k_{dbias}$ kg/m³ are flowtube specific calibration constants valid for specific flowtube operating pressure and gas density ranges, f is the natural frequency of the flowtube 215 in Hertz, $P_0$ is a reference pressure in barA, $P_i$ is the inlet pressure in barA, and T is the temperature of the flowtube in degrees Celsius, $D_2$ and $D_4$ are flowtube-specific calibration constants. C and D are flowtube-type specific temperature compensation parameters. A more general equation to correct the apparent bulk density for pressure is as follows, where $k_{pd2}$ and $k_{pd4}$ are flowtube-specific calibration constants:

$$T_0 = 20.0° \text{ C.}$$

$$\Delta T = T - T_0$$

$$\Delta P = P_i - P_0$$

$$\rho_p = \frac{256}{f^2} \cdot D_2 \cdot (1 + C \cdot \Delta T) \cdot (1 + k_{pd2}\Delta P) + D_4 \cdot (1 + D \cdot \Delta T) \cdot (1 + k_{pd4}\Delta P).$$

One or more apparent intermediate values associated with the multi-phase process fluid are determined based on the first apparent property (520). In general, the apparent intermediate value (or values) is a value related to the multi-phase fluid that includes inaccuracies resulting from the inclusion of more than one phase in the multi-phase fluid. The apparent intermediate value may be, for example, a volume fraction of the multi-phase process fluid. The volume fraction may be a liquid volume fraction that specifies the portion of the multi-phase fluid that is a non-gas. The volume fraction also may be a gas volume fraction that specifies the portion of the multi-phase fluid that is a gas. In general, the volume fraction is a dimensionless quantity that may be expressed as a percentage. The gas volume fraction also may be referred to as a void fraction. If the multi-phase fluid includes liquids and gases, the liquid and gas volume fractions add up to 100%. In other implementations, the apparent intermediate values may be a volumetric flowrate of the multi-phase fluid.

In one implementation, the apparent intermediate values are the apparent volumetric flowrate and the apparent liquid volume fraction and are determined based on the apparent bulk mass flowrate and the apparent bulk density. The apparent volumetric flowrate in m³/s may be determined from the following equation:

$$v_m^a = \frac{m_m^a}{\rho_m^a}.$$

The apparent liquid volume fraction, which is expressed as a percentage, may be determined from the following equation, where $\rho_l$ is the estimated density of the liquid phase of the multi-phase process fluid, and $\rho_g$ is the estimated density of the gas phase of the multi-phase process fluid:

$$LVF^a = \frac{\rho_m^a - \rho_g}{\rho_l - \rho_g} \cdot 100\% = 100 - GVF^a.$$

The estimates of the densities of the liquid and gas phases of the multi-phase fluid may be determined as discussed below. In this example, the multi-phase fluid includes two liquid phases (for example, a first liquid that is water and a second liquid that is a condensate) and a gas phase. However, similar calculations may be performed for other multi-phase fluids. In the equations below, $\rho_{l0}$ kg/m³ is the base liquid density at a known temperature, $T_{l0}°$ C., and $k_l/°$ C. is a coefficient that provides a linear correction to this density as a function of temperature difference from the base temperature $T_{l0}$, are known from knowledge of the particular substances that are included in the multi-phase fluid. The component fluid densities $\rho_{l1}, \rho_{l2}$ kg/m³ at the current fluid temperature may be determined by:

$$\rho_{l1} = \rho_{l10} \cdot (1 + k_{l1} \cdot (T - T_{l10})).$$

$$\rho_{l2} = \rho_{l20} \cdot (1 + k_{l2} \cdot (T - T_{l20})).$$

In some implementations, the user may input the volumetric flow fraction (x) of the first liquid. In other implementations, the volumetric flow fraction may be assumed. In still other implementations, the volumetric flow fraction may be estimated. In some implementations, the volumetric flow fraction may be provided by a user, or the volumetric flow fraction may be obtained from a water-cut measuring device such as a water-cut meter.

Assuming no slip between liquid phases, the volumetric flow fraction of the first liquid $x_l$ % may be determined by:

$$x_1 = \left(\frac{\rho_l - \rho_{l2}}{\rho_{l1} - \rho_{l2}}\right) \cdot 100\%.$$

Using $x_l$ %, and assuming no slip between liquid phases, the combined liquid density (i.e., liquid density of the liquid mixture) may be calculated with:

$$\rho_l = \rho_{l2} + \frac{x_1}{100} \cdot (\rho_{l1} - \rho_{l2})$$

or $$\rho_l = \frac{x_1}{100} \cdot \rho_{l1} + \left(1 - \frac{x_1}{100}\right)\rho_{l2}.$$

Additionally, an estimate of the gas density $\rho_g$ kg/m³ at line conditions of pressure $P_i$ barA and $T_i°$ C. at the inlet the Coriolis flowtube may be determined given a reference density of the gas $\rho_{g0}$ kg/m³ at a reference pressure $P_{g0}$ barA and reference temperature $T_{g0}°$ C. While there are a number of equations of state that take into account compressibility and other non-idealities, the estimate of the actual gas density using the ideal gas laws is assumed to be sufficient and the density of the gas phase may be estimated based on:

$$\rho_g = \rho_{g0} \cdot \frac{P_i}{P_{g0}} \cdot \left(\frac{T_{g0} + 273.15}{T_i + 273.15}\right) \cdot \left(\frac{1}{Z_f}\right).$$

In the above equation, $Z_f$ is the compressibility of the gas in the gas phase, and for some gases (such as natural gas), the compressibility varies with pressure according to the following equation:

$$Z_f = Z_{f0} + k_{zp} \cdot (P - P_0).$$

Models of the gas properties may be generated on-line or off-line using, for example, American Gas Association (AGA) equations.

One or more corrected intermediate values are determined based on a mapping between the apparent intermediate value and the corrected intermediate value (525). For example, the corrected intermediate value may be a corrected liquid volume fraction, $LVF^c$ (%), and/or a corrected volumetric flow, $v_m^c$, m³/s. In one particular implementation, the corrected intermediate values are a corrected liquid volume fraction and a corrected volumetric flowrate that are corrected from the apparent liquid volume fraction and the apparent volumetric flowrate.

The mapping may be a neural network, a statistical model, a polynomial, a function, or any other type of mapping. The neural network or other mapping may be trained with data obtained from a multi-phase fluid for which values of the constituent phases are known. In one implementation, the mapping is a neural network that takes as inputs the apparent liquid volume fraction, the apparent volumetric flowrate, the pressure at the inlet of the vibratable flowtube, and the differential pressure across the vibratable flowtube. The neural network produces a corrected liquid volume fraction and a corrected volumetric flowrate.

In one implementation, prior to inputting an apparent intermediate value into the mapping, the apparent intermediate value may be filtered or conditioned to reduce measurement and process noise. For example, linear filters may be applied to the apparent intermediate value to reduce measurement noise. The time constant of the linear filter may be set to a value that reflects the response time of the measurement instrumentation (e.g., 1 second) such that the filter remains sensitive to actual changes in the fluid flowing through the flowtube (such as slugs of non-gas fluid) while also being able to reduce measurement noise.

The development of a mapping for correcting or improving a multiphase measurement may involve the collection of data under experimental conditions, where the true or reference measurements are provided by additional calibrated instrumentation. Generally, it is not practical to carry out experiments covering all conceivable multi-phase conditions, either due to limitations of the test facility, and/or the cost and time associated with carrying out possibly thousands of experiments. Additionally, it is rarely possible to maintain multiphase flow conditions exactly constant for any extended period of time, due to the inherently unstable flow conditions that occur within multiphase conditions. Accordingly, it is usually necessary to calculate the average values of all relevant parameters, including apparent and true or reference parameter values, over the duration of each experiment, which may typically be of 30 s to 120 s duration. Thus, the mapping may be constructed from experimental data where each data point is derived from the average of for example 30 s to 120 s duration of data.

Difficulties might arise when applying the resulting mapping in the meter during multiphase flow in real time, whereby the particular parameter values observed within the meter are not included in the mapping provided from the previously collected experimental data. There are two primary ways in which this may occur. In the first instance, although the conditions experienced by the meter, averaged over a timescale of about 15 to 120 seconds, do correspond to conditions covered by the mapping, the instantaneous parameter values may fall outside of the region, due to measurement noise and or instantaneous variations in actual conditions due to the instabilities inherent in multiphase flow. As described above, this effect can to some extent be reduced by time-averaging or filtering the parameters used as inputs into the mapping function, though there is a tradeoff between the noise reduction effects of such filtering and the responsiveness of the meter to actual changes in conditions within the multiphase flow. Alternatively, averaged parameter values may fall outside of the mapping because, for instance, it has not been economically viable to cover all possible multiphase conditions during the experimental stage.

It may not be beneficial to apply a mapping function (whether neural net, polynomial or other function) to data that falls outside of the region for which the mapping was intended. Application of the mapping to such data may result in poor quality measurements being generated. Accordingly, jacketing procedures may be applied to ensure that the behavior of the mapping procedure is appropriate for parameter values outside the mapped region, irrespective of the reasons for the parameters falling outside the mapped region. Data that is included in the region may be referred to as suitable data.

Thus, the apparent intermediate values may be "jacketed" prior to inputting the apparent intermediate values into the mapping. For implementations that include one input to the mapping, the region of suitable data may be defined by one or more limits, a range, or a threshold. In other implementations, there may be more than one input to the mapping. In these implementations, the region of suitable data may be defined by a series of lines or planes. Accordingly, as the number of inputs to the mapping increases, defining the region of suitable data becomes more complex. Thus, it may be desirable to use fewer inputs to the mapping. Additionally, using fewer inputs to the mapping may result in a simpler mapping, which may help reduce the computational resources used by the mapping and help increase the speed of determining corrected intermediate values based on the mapping.

Figure 6:
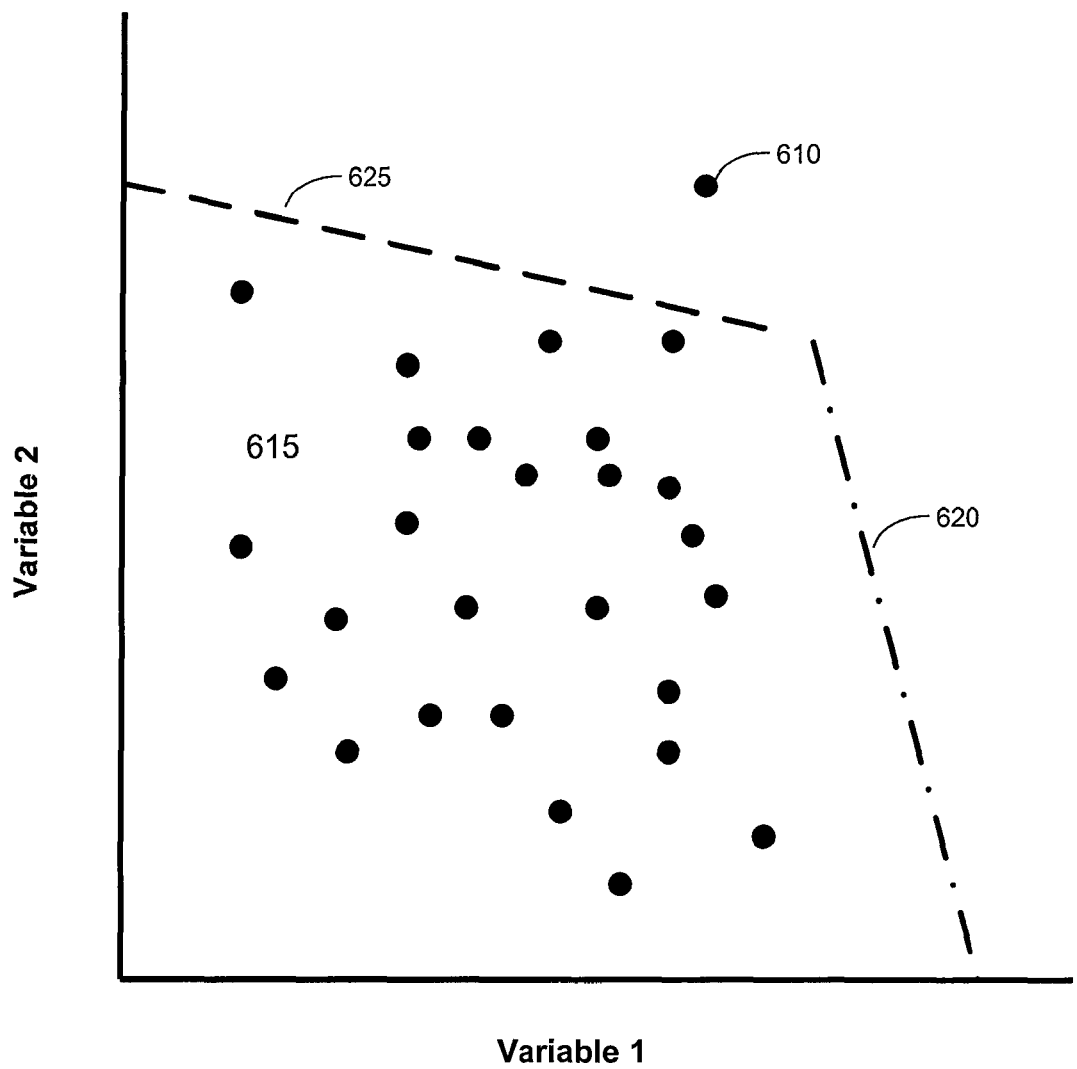
FIG. 6 is an illustration of jacketing.

Referring briefly to FIG. 6, an illustration of jacketing is shown. In this example, an apparent intermediate value 610 having a value that is outside of the defined region 615 may be determined to be unsuitable for input to the mapping. In general, rules are defined to correct an apparent intermediate value that is determined to be outside of the defined region 615. In the example shown in FIG. 6, the intermediate value 615 is defined by the values of two variables, variable 1 and variable 2 (which may be, for example, the liquid volume fraction and the volumetric flow). Thus, the intermediate value is two-dimensional data. The defined region 615 is defined by the lines 620 and 625. However, in other examples, the defined region 615 may be defined by one or more curves, or more than two lines. In other examples, the intermediate value may be higher-order data, and in these examples, the defined region may be defined by a series of surfaces.

For example, an apparent intermediate value that is outside of the defined region 615 (such as the apparent intermediate value 610) may be ignored by the mapping (e.g., the apparent intermediate value is not corrected by the mapping), the apparent intermediate value may not be input to the mapping at all, a fixed correction may be applied to the apparent intermediate value rather than a correction determined by the mapping, or the correction corresponding to the correction that would apply to the value closest to the apparent intermediate value may be applied. Other rules for correcting an apparent intermediate value that is outside of the defined region may be implemented. In general, the jacketing is specific to a particular mapping and is defined for each mapping.

Similar to the jacketing described above, the corrected apparent value may be jacketed, or otherwise checked, prior to using it in further processing.

Referring again to FIG. 5A, one or more estimated phase-specific properties of the multi-phase process fluid may be determined based on the corrected intermediate value or values (530). Using one or more of the apparent intermediate values discussed above rather than a value directly from the flowtube (e.g., an apparent bulk mass flowrate of the multi-phase liquid) may improve the accuracy of the process 500A as compared to, for example, using the first apparent property directly. The phase-specific property may be, for example, a mass flowrate and/or a density of the non-gas and gas phases of the multi-phase fluid. The following equations illustrate the determination of the estimated phase-specific mass flowrates of the constituent phases of the multi-phase process fluid based on the corrected mixture volumetric flowrate and the corrected liquid volume fraction.

The corrected volume faction of the gas phase, $GVF^c$ expressed as a percentage, may be determined from:

$$GVF^c = 100 - LVF^c \%.$$

The phase-specific volumetric flowrate of the gas phase in m³/s may be determined from the following, where $v_m^c$ is the corrected mixture volumetric flow as discussed above with respect to (525):

$$v_g^c = GVF^c \cdot v_m^c.$$

The phase-specific mass flowrate of the gas phase of the multi-phase process fluid may be determined from the following equation:

$$m_g^c = \rho_g \cdot v_g^c = \rho_{g0} \cdot sv_g^c,$$

where the corrected standard volumetric flow $sv_g^c$, of the gas at defined standard conditions of temperature and pressure where it has density $\rho_{g0}$ is given by $$sv_g^c = \frac{\rho_g}{\rho_{g0}} v_g^c.$$

The phase-specific mass flowrate also may be determined for the non-gas phases of the multi-phase process fluid (both the liquid mixture and specific liquid components). Continuing the example above, the multi-phase process fluid has a gas phase and two liquid phases. The corrected volumetric flowrates (m³/s) of the liquid mixture and the specific liquid phases may be determined from the following equation, where $v_m^c$ is the corrected mixture volumetric flow as discussed above with respect to (525):

$$v_l^c = \frac{LVF^c}{100} \cdot v_m^c$$

$$v_{l1}^c = \frac{x_1}{100} \cdot v_l^c$$

$$v_{l2}^c = \left(1 - \frac{x_1}{100}\right) \cdot v_l^c = v_l^c - v_{l1}^c.$$

The phase-specific mass flowrate of the first and second liquid phases (and the liquid mass flowrate) may then be determined from the following equations:

$$m_l^c = \rho_l v_l^c$$

$$m_{l1}^c = \rho_{l1} v_{l1}^c.$$

$$m_{l2}^c = \rho_{l2} v_{l2}^c$$

Thus, the process 500A may produce estimates of the mass flowrates of the constituent phases included in a multi-phase process fluid, with the estimates being based on apparent properties of the multi-phase process fluid obtained from the motion of the flowtube 215.

Referring to FIG. 5B, the estimated phase-specific properties described above are used in an example process 500B to determine corrected phase-specific properties of a multi-phase process fluid based on a measure of wetness and a second apparent property of the multi-phase fluid. The measure of wetness generally indicates the amount of moisture in the multi-phase process fluid, and the measure of wetness may be a Lockhart-Martinelli parameter. The second apparent property is an apparent property of the multi-phase process fluid that is determined from passing the fluid through the differential pressure flowmeter 304, such as an orifice plate. The second apparent property may be an apparent bulk mass flowrate of the multi-phase process fluid. For example, when an orifice plate is used in a wet gas environment, the second apparent property may be the mass flowrate of the fluid as if it were a dry gas (e.g., a gas that does not include liquid).

A multi-phase process fluid is passed through the differential pressure flowmeter 304 (560) and a second apparent property is determined using the differential pressure flowmeter 304 (565). The differential pressure flowmeter may be an orifice plate, as described above with respect to FIG. 3. In other implementations, the differential pressure flowmeter may be a Venturi flowmeter or a V-cone flowmeter. In still other implementations, any obstruction to the flow whose characteristics can be determined may be used. Additionally or alternatively, other types of flowmeters may be used. For example, flowmeters based on vortex, turbine, electromagnetic, or ultrasonic phenomena may be used. Moreover, other differential pressure devices may be used.

The second apparent property is an apparent property of the multi-phase process fluid determined by the differential pressure flowmeter. In one implementation, the second apparent property is the mass flowrate of the multi-phase fluid determined by an orifice plate as if the fluid were a dry gas. Like the Coriolis meter, the differential pressure flowmeter will also produce inaccurate results when a multi-phase process fluid is present. In particular, an orifice plate may assume that the multi-phase fluid is a dry gas. Thus, the readings from the orifice plate for a multi-phase fluid are inaccurate and generally represent the mass flowrate of the multi-phase fluid as if it were a dry gas.

A measure of wetness of the multi-phase process fluid is determined based on the one or more estimated phase-specific properties that were determined based on the one or more corrected intermediate values (570). Although the discussion below uses the same symbols for density, it is understood that the densities at the differential flowmeter and the Coriolis flowmeter may differ. The measure of wetness of the multi-phase process fluid may be a Lockhart-Martinelli parameter, which is determined from the following equation, where $\rho_g$ is the estimated density at the differential pressure flowmeter 304 of the gas included in the gas phase of the multi-phase process fluid, $\rho_l$ is the estimated density of the liquid at the differential pressure flowmeter 304 included in the liquid phase of the multi-phase process fluid, $m_l$ is the estimated mass flowrate of the liquid phase determined from process 500A, and $m_g$ is the estimated mass flowrate of the gas phase determined from process 500A:

$$X_{L-M} = \frac{v_l}{v_g} \sqrt{\frac{\rho_l}{\rho_g}} = \frac{m_l}{m_g} \sqrt{\frac{\rho_g}{\rho_l}}.$$

The estimated densities of the gas and liquid phases can be determined in a manner similar to the manner described with respect to operation 520 of process 500A, except for using the temperature and pressure conditions at the differential pressure flowmeter 304 rather than those conditions at the Coriolis flowmeter 306.

One or more corrected phase-specific properties of the constituent phases of the multi-phase process fluid are determined based on the second apparent property and the measure of wetness (575). Continuing the example above, particularly when the fluid is a wet gas, the second apparent property may be the mass flowrate of the multi-phase process fluid as a dry gas, and the measure of wetness may be the Lockhart-Martinelli parameter. The corrected phase-specific properties may be the mass flowrates of the gas and non-gas phases of the multi-phase process fluid. The corrected mass flowrate of the gas phase and the corrected mass flowrate of the liquid phase may be respectively determined from the Murdock correction equations below, where $m_{gTP}$ is the apparent bulk mass flowrate of the multi-phase process fluid measured by the differential pressure meter:

$$m_g^c = \frac{m_{gTP}}{1 + 1.26 X_{L-M}}$$

$$m_l^c = X_{L-M}^c \cdot m_g^c \cdot \sqrt{\frac{\rho_l}{\rho_g}}.$$

When more than one liquid is included in the liquid phase, the mass flowrates of the specific liquid components may be determined using the following:

$$m_{l1}^c = \rho_{l1} v_{l1}^c,$$

$$m_{l2}^c = \rho_{l2} v_{l2}^c$$

where $v_{l1}^c$ is the corrected volumetric flowrate of the first liquid, and $v_{l2}^c$ is the corrected volumetric flowrate of the second liquid, all of which may be calculated as follows:

$$v_l^c = \frac{m_l^c}{\rho_l}$$

$$v_{l1}^c = \frac{x_1}{100} \cdot v_l^c$$

$$v_{l2}^c = \left(1 - \frac{x_1}{100}\right) \cdot v_l^c,$$

Where $x_1$ is the known measured or assumed volumetric flow fraction of fluid component 1 as before.

The Murdock correction is further described in Murdock, J. W., "Two-phase flow with orifices," Journal of Basic Engineering, ASME Transactions 84 (4), pp 419-433, December 1962.

As an alternative, particularly when the fluid is a wet gas, the corrected mass flowrate of the gas phase and the corrected mass flowrate of the liquid phase may be respectively determined from the Chisholm correction equations below:

$$m_g = \frac{m_{gTP}}{\sqrt{1 + C \cdot X_{L-M} + X_{L-M}^2}}$$

$$= \frac{m_{gTP}}{\sqrt{1 + X_{L-M} \cdot (C + X_{L-M})}}$$

where $$C = \left(\frac{\rho_l}{\rho_g}\right)^{0.25} + \left(\frac{\rho_g}{\rho_l}\right)^{0.25} \text{ (for } X_{L-M} < 1\text{)}.$$

Additionally, the corrected mass flowrate of the liquid phases may be determined based on the following equations, which are described above:

$$m_{l1}^c = \rho_{l1} v_{l1}^c$$

$$m_{l2}^c = \rho_{l2} v_{l2}^c$$

$$v_l^c = \frac{m_l^c}{\rho_l}$$

$$v_{l1}^c = \frac{x_1}{100} \cdot v_l^c$$

$$v_{l2}^c = \left(1 - \frac{x_1}{100}\right) \cdot v_l^c.$$

The Chisholm correction is described further in Chisholm, D., "Flow of incompressible two-phase mixtures through sharp-edged orifices," IMechE Journal of Mechanical Engineering Science, Vol 9, No 1, pp 72:78 February 1967 and Chisholm, D., "Research Note: Two-phase flow through sharp-edged orifices," IMechE Journal of Mechanical Engineering Science, Volume 19, No 3, pp 128:130 June 1977.

In other implementations, other corrections may be used as appropriate depending on the type of differential pressure flowmeter used. For instance, if a Venturi flowmeter is used, then the De Leeuw correction may be used. This correction is similar in form to the Chisholm correction with modified coefficients. See, for example, De Leeuw, H., "Wet Gas Flow Measurement using a combination of Venturi meter and a tracer technique," North Sea Flow Measurement Workshop, Peebles, Scotland, October 1994 and De Leeuw, H., "Liquid Correction of Venturi Meter Readings in Wet Gas Flow", North Sea Flow Measurement Workshop, Norway, October 1997.

The corrected phase-specific properties determined in (575) are compared to the estimated phase-specific properties determined in (530) (580). Comparing the phase-specific properties determined in (530), which are determined based on data from a Coriolis meter, to those determined in (575), which are determined based on data from a Coriolis meter and a differential pressure meter, allows an assessment of whether the instruments are performing properly. For example, if the phase-specific properties are compared and found to be similar, it is generally an indication that the Coriolis meter and the differential pressure meter are performing properly.

The calculations described in the various implementations may be performed by the transmitter of the Coriolis flowmeter, by a computing device coupled to the Coriolis meter and/or the differential pressure flowmeter, or by a flow computer or computing device coupled to the Coriolis flowmeter and the differential pressure flowmeter.

A number of implementations have been described. Nevertheless, it will be understood that various modifications may be made. Accordingly, other implementations are within the scope of the following claims.

What is claimed is:

1. A method comprising:
    passing a multi-phase process fluid through a vibratable flowtube and a differential pressure flowmeter;
    inducing motion in the vibratable flowtube;
    determining a first apparent property of the multi-phase process fluid based on the motion of the vibratable flowtube;
    determining one or more apparent intermediate values associated with the multi-phase process fluid based on the first apparent property;
    determining one or more corrected intermediate values based on a mapping between the apparent intermediate values and the corrected intermediate values;
    determining one or more estimated phase-specific properties of the multi-phase process fluid based on the corrected intermediate values;
    determining a measure of wetness of the multi-phase process fluid based on the one or more estimated phase-specific properties;

determining a second apparent property of the multi-phase process fluid using the differential pressure flowmeter; and determining a corrected phase-specific property of a phase of the multi-phase process fluid based on the measure of wetness and the second apparent property.

2. The method of claim 1, wherein the mapping is a neural network.

3. The method of claim 1, wherein the multi-phase process fluid is a wet gas.

4. The method of claim 1, wherein:
determining the first apparent property of the multi-phase process fluid includes determining a third apparent property of the multi-phase process fluid based on the motion of the vibratable flowtube; and determining one or more apparent intermediate values associated with the multi-phase process fluid based on the first apparent property comprises determining one or more apparent intermediate values associated with the multi-phase process fluid based on the first apparent property and the third apparent property.

5. The method of claim 4, wherein the first apparent property of the multi-phase process fluid is an apparent bulk mass flowrate of the multi-phase process fluid and the third apparent property is an apparent bulk density of the multi-phase process fluid.

6. The method of claim 1, wherein determining one or more apparent intermediate values associated with the multi-phase process fluid based on the first apparent property includes determining a volume fraction of the multi-phase process fluid and a volumetric flowrate of the multi-phase process fluid.

7. The method of claim 1, further comprising receiving one or more measurements corresponding to an additional property of the multi-phase process fluid.

8. The method of claim 7, wherein
the additional property of the multi-phase process fluid includes one or more of a temperature of the multi-phase process fluid, a pressure associated with the multi-phase process fluid, or a water-cut of the multi-phase process fluid, and determining one or more apparent intermediate value associated with the multi-phase process fluid based on the first apparent property includes determining the one or more apparent intermediate values based on the first apparent property and the additional property.

9. The method of claim 1, wherein the measure of wetness is a Lockhart-Martinelli parameter.

10. The method of claim 1, wherein the second apparent property is a mass flowrate of the multi-phase process fluid as a dry gas.

11. The method of claim 1, wherein the differential pressure flowmeter is an orifice plate.

12. The method of claim 1, wherein determining a phase-specific property of the multi-phase process fluid based on the measure of wetness and the second apparent property includes determining a mass flowrate of a gas phase of the multi-phase process fluid.

13. A flowmeter comprising:
a vibratable flowtube, the flowtube being configured to receive a multi-phase process fluid;
a driver connected to the flowtube and configured to impart motion to the flowtube such that the flowtube vibrates;
a sensor connected to the flowtube and configured to sense the motion of the flowtube and generate a sensor signal; and a controller to receive the sensor signal and configured to:
determine a first apparent property of the multi-phase process fluid based on the motion of the vibratable flowtube;
determine one or more apparent intermediate values associated with the multi-phase process fluid based on the first apparent property;
determine one or more corrected intermediate values based on a mapping between the apparent intermediate values and the corrected intermediate values;
determine one or more estimated phase-specific properties of the multi-phase process fluid based on the corrected intermediate values;
determine a measure of wetness of the multi-phase process fluid based on the one or more estimated phase-specific properties;
receive a second apparent property of the multi-phase process fluid, the second apparent property being determined using a differential pressure flowmeter; and
determine a corrected phase-specific property of a phase of the multi-phase process fluid based on the measure of wetness and the second apparent property.

14. The flowmeter of claim 13, wherein the mapping is a neural network.

15. The flowmeter of claim 13, wherein the multi-phase process fluid is a wet gas.

16. The flowmeter of claim 13, wherein the controller is further configured to:
determine that the first apparent property of the multi-phase process fluid includes determining a third apparent property of the multi-phase process fluid based on the motion of the vibratable flowtube; and
determine that one or more apparent intermediate values associated with the multi-phase process fluid based on the first apparent property comprises determining one or more apparent intermediate values associated with the multi-phase process fluid based on the first apparent property and the third apparent property.

17. The flowmeter of claim 13, wherein to determine one or more apparent intermediate values associated with the multi-phase process fluid based on the first apparent property, the controller is configured to determine a volume fraction of the multi-phase process fluid and a volumetric flowrate of the multi-phase process fluid.

18. The flowmeter of claim 13, wherein the controller is further configured to receive one or more measurements corresponding to an additional property of the multi-phase process fluid.

19. The flowmeter of claim 13, wherein the measure of wetness is a Lockhart-Martinelli parameter.

20. The flowmeter of claim 13, wherein the second apparent property is a mass flowrate of the multi-phase process fluid as a dry gas.

21. The flowmeter of claim 13, wherein to determine a phase-specific property of the multi-phase process fluid based on the measure of wetness and the second apparent property, the controller is configured to determine a mass flowrate of a gas phase of the multi-phase process fluid.

22. A flowmeter transmitter for use with a vibratable flowtube coupled to a differential pressure flowmeter such that a multi-phase process fluid passes through the vibratable flowtube and the differential pressure flowmeter, the flowmeter transmitter comprising:

at least one processing device; and a storage device, the storage device storing instructions for causing the at least one processing device to:

induce motion in the vibratable flowtube, the vibratable flowtube being configured to receive a multi-phase process fluid;

determine a first apparent property of the multi-phase process fluid based on the motion of the vibratable flowtube;

determine one or more apparent intermediate values associated with the multi-phase process fluid based on the first apparent property;

determine one or more corrected intermediate values based on a mapping between the apparent intermediate values and the corrected intermediate values;

determine one or more estimated phase-specific properties of the multi-phase process fluid based on the corrected intermediate values;

determine a measure of wetness of the multi-phase process fluid based on the one or more estimated phase-specific properties;

receive a second apparent property of the multi-phase process fluid, the second apparent property being determined using a differential pressure flowmeter; and determine a corrected phase-specific property of a phase of the multi-phase process fluid based on the measure of wetness and the second apparent property.

23. The transmitter of claim 22, wherein the multi-phase process fluid is a wet gas.

24. The transmitter of claim 22, wherein the measure of wetness is a Lockhart-Martinelli parameter.

25. The transmitter of claim 22, wherein the instructions further include instructions for causing the at least one processing device to receive one or more measurements corresponding to an additional property of the multi-phase process fluid.

26. A system comprising:

a vibratable flowtube configured to receive a multi-phase process fluid;

a differential pressure flowmeter coupled to the vibratable flowtube; and one or more processing devices configured to:

induce motion in the vibratable flowtube;

determine a first apparent property of the multi-phase process fluid based on the motion of the vibratable flowtube;

determine one or more apparent intermediate values associated with the multi-phase process fluid based on the first apparent property;

determine one or more corrected intermediate values based on a mapping between the apparent intermediate values and the corrected intermediate values;

determine one or more estimated phase-specific properties of the multi-phase process fluid based on the corrected intermediate values;

determine a measure of wetness of the multi-phase process fluid based on the one or more estimated phase-specific properties;

receive a second apparent property of the multi-phase process fluid, the second apparent property being determined using the differential pressure flowmeter; and determining a corrected phase-specific property of a phase of the multi-phase process fluid based on the measure of wetness and the second apparent property.

27. The system of claim 26, wherein:

to determine the first apparent property of the multi-phase process fluid, the one or more processing devices are configured to determine a third apparent property of the multi-phase process fluid based on the motion of the vibratable flowtube; and to determine one or more apparent intermediate values associated with the multi-phase process fluid based on the first apparent property, the one or more processing devices are configured to determine one or more apparent intermediate values associated with the multi-phase process fluid based on the first apparent property and the third apparent property.

28. The system of claim 26, wherein the one or more processing devices are further configured to receive one or more measurements corresponding to an additional property of the multi-phase process fluid.

29. The system of claim 28, wherein:

the additional property of the multi-phase process fluid includes one or more of a temperature of the multi-phase process fluid, a pressure associated with the multi-phase process fluid, or a water-cut of the multi-phase process fluid, and to determine one or more apparent intermediate value associated with the multi-phase process fluid based on the first apparent property, the one or more processing devices are configured to determine the one or more apparent intermediate values based on the first apparent property and the additional property.

30. The system of claim 26, wherein to determine a phase-specific property of the multi-phase process fluid based on the measure of wetness and the second apparent property, the one or more processing devices are configured to determine a mass flowrate of a gas phase of the multi-phase process fluid.

* * * * *